US010729496B2

(12) United States Patent
Hunziker et al.

(10) Patent No.: US 10,729,496 B2
(45) Date of Patent: Aug. 4, 2020

(54) DERMATOLOGICAL PICOSECOND LASER TREATMENT SYSTEMS AND METHODS USING OPTICAL PARAMETRIC OSCILLATOR

(71) Applicant: Cutera, Inc., Brisbane, CA (US)

(72) Inventors: Lukas E. Hunziker, San Jose, CA (US); Michael A. Karavitis, San Pedro, CA (US); Hsiao-Hua Liu, Brisbane, CA (US)

(73) Assignee: Cutera, Inc., Brisbane, CA (US)

( * ) Notice: Subject to any disclaimer, the term of this patent is extended or adjusted under 35 U.S.C. 154(b) by 281 days.

(21) Appl. No.: 15/820,421

(22) Filed: Nov. 21, 2017

(65) Prior Publication Data

US 2019/0151019 A1    May 23, 2019

(51) Int. Cl.
| | |
|---|---|
| *A61B 18/20* | (2006.01) |
| *H01S 3/00* | (2006.01) |
| *G02F 1/35* | (2006.01) |
| *H01S 3/06* | (2006.01) |
| *H01S 3/11* | (2006.01) |
| *A61B 17/00* | (2006.01) |
| *A61B 18/00* | (2006.01) |

(52) U.S. Cl.
CPC .......... *A61B 18/203* (2013.01); *G02F 1/3532* (2013.01); *H01S 3/0057* (2013.01); *H01S 3/0092* (2013.01); *H01S 3/0602* (2013.01); *H01S 3/11* (2013.01); *A61B 2017/00154* (2013.01); *A61B 2017/00769* (2013.01); *A61B 2018/00452* (2013.01); *A61B 2018/2075* (2013.01)

(58) Field of Classification Search
None
See application file for complete search history.

(56) References Cited

U.S. PATENT DOCUMENTS

| | | | |
|---|---|---|---|
| 5,017,806 A | 10/1991 | Cheng et al. | |
| 5,066,291 A | 11/1991 | Stewart | |
| 5,117,126 A | 5/1992 | Geiger | |
| 5,365,366 A | 11/1994 | Kafka et al. | |
| 5,454,808 A * | 10/1995 | Koop ............... | A61B 18/201 606/17 |
| 5,520,679 A | 5/1996 | Lin | |
| 5,556,372 A | 9/1996 | Talish et al. | |
| 5,579,152 A | 11/1996 | Ellingson et al. | |

(Continued)

FOREIGN PATENT DOCUMENTS

| | | |
|---|---|---|
| WO | 2007127924 A2 | 11/2007 |
| WO | 2008039557 A1 | 4/2008 |

(Continued)

OTHER PUBLICATIONS

Arisholm, Gunnar et al., "Limits to the Power Scalability of High-Gain Optical Parametric Amplifiers", J. Opts. Soc. Am B/vol. 21, No. 3, Mar. 2004, pp. 578-590, US.

(Continued)

*Primary Examiner* — Brian T Gedeon
(74) *Attorney, Agent, or Firm* — Timothy L. Scott

(57) ABSTRACT

Dermatological systems and methods for providing a picosecond laser treatment a plurality of treatment wavelengths, at least one of which is provide by an optical parametric oscillator (OPO).

29 Claims, 9 Drawing Sheets

(56) References Cited

U.S. PATENT DOCUMENTS

| | | | |
|---|---|---|---|
| 5,594,592 A * | 1/1997 | Harlamoff | G02F 1/39 |
| | | | 359/330 |
| 5,619,517 A | 4/1997 | Dixon | |
| 5,634,922 A | 6/1997 | Hirano et al. | |
| 5,661,595 A | 8/1997 | Stamm et al. | |
| 5,687,186 A | 11/1997 | Stultz | |
| 5,742,626 A | 4/1998 | Mead et al. | |
| 5,752,949 A * | 5/1998 | Tankovich | A61B 18/1442 |
| | | | 606/133 |
| 5,754,333 A | 5/1998 | Fulbert et al. | |
| 5,782,822 A | 9/1998 | Blake et al. | |
| 5,841,798 A | 11/1998 | Chen et al. | |
| 5,885,211 A | 3/1999 | Eppstein et al. | |
| 5,896,220 A | 4/1999 | Stamm et al. | |
| 5,995,522 A | 11/1999 | Scherrer et al. | |
| 5,999,547 A | 12/1999 | Schneider et al. | |
| 6,016,214 A * | 1/2000 | Meyer, Jr. | G02F 1/39 |
| | | | 359/237 |
| 6,044,094 A | 3/2000 | Govorkov | |
| 6,101,022 A | 8/2000 | Chen et al. | |
| 6,142,939 A | 11/2000 | Eppstein et al. | |
| 6,215,800 B1 | 4/2001 | Komine | |
| 6,241,720 B1 | 6/2001 | Nighan, Jr. et al. | |
| 6,295,160 B1 | 9/2001 | Zhang et al. | |
| RE37,504 E | 1/2002 | Lin | |
| 6,358,243 B1 | 3/2002 | Esterowitz et al. | |
| 6,433,918 B1 | 8/2002 | Kasai et al. | |
| 6,610,049 B2 | 8/2003 | Lai et al. | |
| 6,647,034 B1 | 11/2003 | Smith et al. | |
| 6,963,443 B2 | 11/2005 | Pfeiffer et al. | |
| 6,991,644 B2 | 1/2006 | Spooner et al. | |
| 7,016,103 B2 | 3/2006 | Paschotta et al. | |
| 7,041,094 B2 | 5/2006 | Connors et al. | |
| 7,208,007 B2 | 4/2007 | Nightingale et al. | |
| 7,211,060 B1 | 5/2007 | Talish et al. | |
| 7,291,140 B2 | 11/2007 | MacFarland et al. | |
| 7,326,199 B2 | 2/2008 | MacFarland et al. | |
| 7,367,341 B2 | 5/2008 | Anderson et al. | |
| 7,410,469 B1 | 8/2008 | Talish et al. | |
| 7,422,599 B2 | 9/2008 | Perez | |
| 7,447,245 B2 | 11/2008 | Caprara et al. | |
| 7,465,307 B2 | 12/2008 | Caprara et al. | |
| 7,524,328 B2 | 4/2009 | Connors et al. | |
| 7,616,304 B2 | 11/2009 | Gankkhanov et al. | |
| 7,618,414 B2 | 11/2009 | Connors et al. | |
| 7,686,839 B2 | 3/2010 | Parker | |
| 7,703,458 B2 | 4/2010 | Levernier et al. | |
| 7,722,600 B2 | 5/2010 | Connors et al. | |
| 7,780,652 B2 | 8/2010 | MacFarland et al. | |
| 7,814,915 B2 | 10/2010 | Davenport et al. | |
| 7,878,206 B2 | 2/2011 | Connors et al. | |
| 7,955,282 B2 | 6/2011 | Doo | |
| 7,998,181 B2 | 8/2011 | Nightingale et al. | |
| 8,094,368 B2 | 1/2012 | Ebrahim-Zadeh et al. | |
| 8,172,835 B2 | 7/2012 | Leyh et al. | |
| 8,211,097 B2 | 7/2012 | Leyh | |
| 8,275,422 B2 | 9/2012 | Allison | |
| 8,276,592 B2 | 10/2012 | Davenport et al. | |
| 8,285,390 B2 | 10/2012 | Levinson et al. | |
| 8,317,780 B2 | 11/2012 | Davenport et al. | |
| 8,353,899 B1 | 1/2013 | Wells et al. | |
| 8,366,703 B2 | 2/2013 | Davenport et al. | |
| 8,380,306 B2 | 2/2013 | Pickett | |
| 8,439,901 B2 | 5/2013 | Davenport et al. | |
| 8,454,591 B2 | 6/2013 | Leyh et al. | |
| 8,460,280 B2 | 6/2013 | Davenport et al. | |
| 8,474,463 B2 | 6/2013 | Levernier et al. | |
| 8,498,043 B2 | 7/2013 | Esteban-Martin et al. | |
| 8,523,927 B2 | 9/2013 | Levinson et al. | |
| 8,562,599 B2 | 10/2013 | Leyh | |
| 8,585,618 B2 | 11/2013 | Hunziker et al. | |
| 8,656,931 B2 | 2/2014 | Davenport et al. | |
| 8,657,811 B2 | 2/2014 | Arai et al. | |
| 8,702,774 B2 | 4/2014 | Baker et al. | |
| 8,834,547 B2 | 9/2014 | Anderson et al. | |
| 8,840,608 B2 | 9/2014 | Anderson et al. | |
| 8,867,122 B2 | 10/2014 | Barr et al. | |
| 8,870,856 B2 | 10/2014 | Connors et al. | |
| 8,891,160 B2 | 11/2014 | Vodopyanov | |
| 8,902,939 B2 | 12/2014 | Kafka et al. | |
| 8,915,906 B2 | 12/2014 | Davenport et al. | |
| 8,920,409 B2 | 12/2014 | Davenport et al. | |
| 8,939,966 B2 | 1/2015 | Hahn | |
| 9,132,031 B2 | 9/2015 | Levinson et al. | |
| 9,308,120 B2 | 4/2016 | Anderson et al. | |
| 9,375,345 B2 | 6/2016 | Levinson et al. | |
| 9,685,753 B2 | 6/2017 | Hellstrom et al. | |
| 9,913,688 B1 | 3/2018 | Karavitis | |
| 10,014,652 B2 * | 7/2018 | Kafka | H01S 3/0071 |
| 10,156,771 B2 | 12/2018 | Woodward, IV et al. | |
| 2002/0013575 A1 | 1/2002 | Lai et al. | |
| 2005/0049582 A1 | 3/2005 | DeBenedictis et al. | |
| 2005/0087198 A1 | 4/2005 | Bruno-Raimondi et al. | |
| 2005/0279369 A1 | 12/2005 | Lin | |
| 2006/0084952 A1 | 4/2006 | Pallikaris et al. | |
| 2006/0282132 A1 | 12/2006 | Arai et al. | |
| 2007/0255362 A1 | 11/2007 | Levinson et al. | |
| 2008/0221560 A1 | 9/2008 | Arai et al. | |
| 2008/0269849 A1 | 10/2008 | Lewis | |
| 2009/0069871 A1 | 3/2009 | Mahadevan-Jansen et al. | |
| 2009/0275927 A1 | 11/2009 | Mahadevan-Jansen et al. | |
| 2009/0304033 A1 * | 12/2009 | Ogilvy | H01S 3/08059 |
| | | | 372/10 |
| 2010/0249893 A1 | 9/2010 | Aller | |
| 2011/0284728 A1 * | 11/2011 | Burdge | G01S 7/4816 |
| | | | 250/216 |
| 2012/0022518 A1 | 1/2012 | Levinson | |
| 2013/0043392 A1 | 2/2013 | Mildren | |
| 2013/0066309 A1 | 3/2013 | Levinson | |
| 2013/0079684 A1 | 6/2013 | Rosen et al. | |
| 2013/0245725 A1 | 9/2013 | Mahadevan-Jansen et al. | |
| 2014/0005760 A1 | 1/2014 | Levinson et al. | |
| 2014/0257443 A1 | 9/2014 | Baker et al. | |
| 2014/0277219 A1 | 9/2014 | Nanda | |
| 2014/0277302 A1 | 9/2014 | Weber et al. | |
| 2014/0296751 A1 | 10/2014 | Greenberg | |
| 2014/0316393 A1 | 10/2014 | Levinson | |
| 2014/0343462 A1 | 11/2014 | Burnet | |
| 2014/0379052 A1 | 12/2014 | Myeong et al. | |
| 2015/0051671 A1 | 2/2015 | Browne et al. | |
| 2015/0202454 A1 | 7/2015 | Burnett | |
| 2015/0265492 A1 | 8/2015 | O'Neil et al. | |
| 2015/0328077 A1 | 11/2015 | Levinson | |
| 2016/0051401 A1 | 2/2016 | Yee et al. | |
| 2016/0310756 A1 | 10/2016 | Boll et al. | |
| 2019/0000529 A1 | 1/2019 | Kothare et al. | |

FOREIGN PATENT DOCUMENTS

| | | |
|---|---|---|
| WO | 2008143678 A1 | 11/2008 |
| WO | 2014149021 A2 | 9/2014 |
| WO | 2014151872 A2 | 9/2014 |

OTHER PUBLICATIONS

Farsun, Oystein et al, "High-Pulse-Energy, Linear Optical Parametric Oscillator with Narrow and Symmetrical Far Field", Optical Society of America, vol. 21, No. 17, Aug. 26, 2013, Optics Express pp. 20171-20178, US.

Keller, Matthew D. et al., "In Vitro Testing of Dual-Mode Thulium Microsurgical Laser", Photonic Therapeutics and Diagnostics VIII, edited by Nikiforos Kollias, et al, Proc. of SPIE vol. 8207, pp. 820711-1 through 820711-8, US.

Rustad, Gunnar et al., "Design of a High Pulse Energy Coherent Ultraviolet Source—Simulations and Experimental Design", Norwegian Defence Research Establishment (FFAI), Feb. 1, 2013, 61 pages, Norway.

Rustad, Gunnar et al., "Effect of Idler Absorption in Pulsed Optical Parametric Oscillators" Optical Society of America, vol. 19, No. 3, Jan. 31, 2011, Optics Express, pp. 2815-2830, US.

(56) References Cited

OTHER PUBLICATIONS

Smith, Arlee V. et al., "Nanosecond Optical Parametric Oscillator with 90 Image Rotation: Design and Performance," Journal of Optical Society of America, vol. 19, No. 8, Aug. 2002, pp. 1801-1814, US.

Vogel, Alfred et al., "Minimization of Thermomechanical Side Effects and Increase of Ablation Efficiency in IR Ablation by Use of Multiply Q-Switched Laser Pulses," Proc. SPIE vol. 4617A, Laser Tissue Interaction XIII, 2002, Germany.

* cited by examiner

DERMATOLOGICAL PICOSECOND LASER TREATMENT SYSTEMS AND METHODS USING OPTICAL PARAMETRIC OSCILLATOR

BACKGROUND OF THE INVENTION

This invention relates generally to the field of electromagnetic-based dermatological treatment systems, and more specifically to systems and methods for treatment of dermatological conditions with lasers having at least one wavelength determined by an optical parametric oscillator.

A variety of dermatological conditions are treatable using electromagnetic radiation (EMR). Sources of EMR for such treatments include lasers, flashlamps, and RF sources, each of which has distinct advantage and disadvantage profiles. EMR devices have been used, for example, treating abnormal pigmentation conditions, body sculpting (e.g., removal of subcutaneous adipose tissue), hair removal, treatment of vascular skin conditions (e.g., spider veins), reduction of wrinkles and fine lines, and dyschromia, among other conditions. Abnormal pigmentation conditions may include tattoos and benign pigmented lesions associated with high local concentrations of melanin in the skin, such as freckles, age spots, birthmarks, lentigines, and nevi, among other pigmentation conditions. Both pulsed and continuous-wave (CW) laser systems have been used to treat pigmentation conditions, although pulsed lasers are more frequently used.

Nanosecond lasers have been used for decades to treat pigmented lesions and tattoo removal. Nanosecond lasers, as used herein, are pulsed lasers having a pulse width (PW) or duration of greater than 1 nanosecond (nsec) up to 1 microsecond ($\mu$sec). By delivering the laser energy in a pulse with a very short time duration, highly localized heating (and destruction) of a tissue target structure (e.g., melanin, ink particles, collagen) can be achieved, thereby minimizing damage to non-target structures. Heating in tissues depends upon both the absorption coefficient of the irradiated tissue structures for the wavelength of laser light used, as well as their thermal relaxation times (TRT), which is a measure of how rapidly the affected structure returns to its original temperature. So long as the laser pulse duration is less than the thermal relaxation time of the target, no significant heat can escape into non-target structures, and damage to non-target structures is limited.

The availability of picosecond laser pulses has ushered in a new paradigm in tattoo removal. As used herein, picosecond lasers are pulsed lasers having a pulse width or duration of 1 picosecond (psec) up to (and preferably below) 1 nsec. Studies have shown that the diameter of tattoo ink particles can range from 35 nm to 200 nm, with clusters as large as 10 $\mu$m. To clear the tattoo ink, the particles must be broken up into smaller fragments that can be cleared by the body. To break the particles up effectively, the laser energy must be delivered within the TRT of the particle, since the energy that escapes into the surrounding tissue not only damages non-target structures but also is unavailable to break down the target structure. A simple dimensional analysis shows that the TRT of a spherical particle scales with the square of its diameter, and ink particles smaller than about 150 nm will have relaxation times below 1 ns.

While the pulse duration for nanosecond lasers is generally less than the TRT for melanin in the skin, the small size of many ink particles in tattoos can result in TRT times of less than 1 nanosecond for those particles. Consequently, the use of conventional Q-switched nanosecond lasers, which produce pulses of 5-20 nsec in duration, may result in ineffective ink removal as well as damage to tissue structures such as blood vessels, collagen, and melanin as the pulsed laser energy escapes into adjacent non-target tissue structures after the lapse of the TRT. This is particularly true for lasers having wavelengths that are highly absorbed by the non-target structures. Studies have shown that the use of picosecond lasers instead of nanosecond lasers can reduce the number of treatment sessions required to clear tattoos by a factor of 3.

Treatment of tattoos and pigmented lesions with picosecond laser pulses is a new and rapidly developing field in dermatology. Although nanosecond lasers are in theory should be adequate for removal of benign pigmented lesions because the relaxation time of melanin is greater than the pulse width for many nanosecond lasers, physicians have reported that lower treatment fluences are required when using picosecond laser pulses, which reduces thermal loading to tissue and the risk of adverse events. Thus, picosecond laser pulses may offer less tissue damage and higher safety margins for pigmented lesions, in addition to their superior performance for tattoo removal. The potential for improved clinical outcomes using picosecond lasers has resulted in commercially available systems having pulse widths of 500-1000 psec with pulse energies (i.e., energy per pulse) exceeding 100 mJ. On the other hand, high-energy picosecond lasers are much more complex and costly than any other energy-based treatment systems in the dermatology market today, and there is a need for more flexible, less expensive picosecond laser systems.

Tattoo removal presents a number of distinct challenges for laser-based pigmentation treatment systems. Tattoos are created by depositing thousands of ink particles below the epidermis into the dermis of the skin. The depth of ink particles may range from 250-750 $\mu$m, or more commonly 300-500 $\mu$m. In some instances, however, ink depths up to 1800 $\mu$m may occur. The wide particle size distribution, as already noted, also presents a challenge for effective tattoo removal while minimizing damage to surrounding structures.

Lasers remove tattoos by breaking down the ink particles that form the tattoo design with laser light at a wavelength that is highly absorbed by the ink used in the tattoo, and at a fluence (energy per area, typically expressed as $J/cm^3$) sufficient to rupture the ink particles into smaller particles that can be removed by the body's natural repair systems.

Ink colors are determined based on their light absorption profile. A given color results from the ink absorbing complementary colors of light, i.e., colors opposite to the ink color on a color wheel. For example, because red and green are complementary colors, green inks appear green to the eye because they absorb colors in the red area of the visible light spectrum, while red inks appear red because they absorb colors in the green area of the visible light spectrum. Thus, green inks are more efficiently removed by red light, since green ink has a relatively high absorption of its complementary color. Conversely, red inks are best removed by green light because they highly absorb light in the green wavelengths.

Tattoos incorporating multiple ink colors present special challenges in laser-based removal systems, because multiple laser wavelengths may be necessary to remove all of the different ink colors. Thus, multiple laser sources may be used in some systems, resulting in systems that are much more expensive, complex, and bulky. To avoid damage to the skin because of the high energy fluences involved, many systems allow a user to vary the width of the laser beam applied to the tattoo.

Shading in tattoos presents another challenge to safe and efficient tattoo removal. Shading results in significant variations in the ink particle density (i.e., color intensity variation) across the tattoo area. Because of this, some systems allow a user to vary the pulse width (PW) of pulsed laser systems, also adding to the complexity of the system. In addition, because the ink particles may be located at different depths within the dermis, it is preferable for the laser light to have a high fluence even at relatively large beam diameters.

The first commercial dermatological picosecond laser systems used either a single 755 nm lasing wavelength, with alexandrite as the lasing medium, or dual 1064 nm and 532 nm laser wavelengths using Nd:YAG lasers. The 755 nm and 1064 nm wavelengths are part of the near-infrared portion of the electromagnetic spectrum, and are well-suited to removal of black tattoo inks due to their broad absorption spectra. The 532 nm wavelength is in the green portion of the visible spectrum, and is well-suited to removal of red inks which strongly absorb green light (the complementary color of red).

Because black and red are the most common tattoo colors, dual wavelength (532 nm and either 755 or 1064 nm) picosecond systems are the most common systems available. However, green and blue inks occur in about one-third of tattoos, and the absorption strength for these inks is greatest in the red portion of the visible spectrum. Accordingly, there is a need for a red wavelength in addition to the dual wavelength 1064/755, 532 nm (near infrared and green) picosecond laser systems to facilitate removal of green and blue inks. In view of the already-high cost of picosecond laser systems, the addition of a red wavelength must be done at a low cost, and in a flexible system that allows different wavelengths of light to be selected quickly and easily.

Because of their versatility, dual wavelength (1064/755, 532) picosecond systems are widely used to treat benign pigmented lesions, which involve the removal of melanin particles from the skin. Pulsed light at 532 nm is highly absorbed by melanin, while 1064 nm light absorbed less than 10% as well (absorption coefficients of 55.5 $mm^{-1}$ and 4.9 $mm^{-1}$) poorly absorbed. In addition, penetration depth of laser light falls rapidly with wavelength. Therefore, 532 nm laser light is effective at aggressive treatment of shallow pigment and 1064 nm light is more commonly used for milder but deeper treatment. It would be useful to have a third wavelength with an intermediate absorption in melanin.

Treatment of pigmented lesions can sometimes result in post-inflammatory hyperpigmentation or hypopigmentation. While the reason for such adverse events is uncertain, it is believed that this may result from injury of the laser light to blood vessels. Accordingly, effective wavelengths for treatment of pigments are those that minimize potential damage to blood vessels in the superficial dermis, and maximize the absorption of melanin relative to hemoglobin.

Pulsed red light has been provided in prior art laser systems, by laser-induced florescence of organic dyes. Typically, excitation is provided by a 532 nm (green light) Nd:YAG pulsed laser, with the red emission wavelength determined by the specific dye being used. Wavelengths of 585, 595, and 650 nm have been provided. Dyes are sometimes provided embedded in a sold substrate. In systems of this type, the minimum pulse duration is defined by the fluorescence lifetime of the dye, which is typically between 1-5 ns, precluding their use in picosecond laser systems. Incoherent (non-laser) light may be captured optically and focused onto a treatment plane.

In other systems, the dye cells may be used as the gain medium in a laser cavity to produce laser emission, in which case picosecond pulses are possible because the pulse duration is approximately equal to that of the excitation laser. However, the cost of assembling such systems is significantly increased relative to systems that do not require dyes, and becomes prohibitive if the dye cells must be replaced frequently.

A more fundamental limitation of dye systems is their susceptibility to optical degradation. Both output energy and beam profile uniformity fall rapidly with operation, typically within 10,000 laser shots or pulses. Fluence of the beam at the treatment plane therefore becomes irregular and continues to change over time, leading to poor clinical outcomes. Emission also tends to have low spatial coherence, making it difficult to deliver the beam through a fiber or articulated are to an applicator, such as a handpiece, for application to the patient.

Because of optical degradation issues, dye cells are typically designed as a consumable item that attaches to the end of the applicator (e.g., a handpiece). While this allows the user to change the dye cell when performance drops, restoring beam uniformity and fluence, it introduces several limitations. First, in multi-wavelength systems the dye cell must be removed to change wavelengths, which is inconvenient to the user and patient during removal of multi-colored tattoos requiring multiple wavelengths in a single treatment session. Second, because the dye cell is near the point of application, integration of photometry to detect the optical degradation is difficult because of space limitations. In spite of these limitations, dye cells have seen limited but consistent use in the field for decades because of their ability to provide multiple laser wavelengths.

Another known method for generating red-wavelength picosecond laser pulses is through second harmonic generation, in which the frequency of the pumping laser is doubled, resulting in an output having wavelengths that are half that of the pumping laser. For example, Nd:YAG lasing wavelengths such as 1319 or 1338 nm may be frequency doubled with nonlinear crystals to produce red picosecond pulses at 659 and 669 nm. However, pumping wavelengths capable of frequency doubling to provide red laser light have relatively low optical gain, making the cost and complexity at these wavelengths significantly greater than existing 1064 and 532 nm dual wavelength systems. In addition, wavelengths in the 1300 nm range have limited use for dermatology, and such systems would have only one wavelength of significant value unless more than one laser engine is provided in the system, which would significantly increase system complexity, cost and bulk. Such systems are not economical and have not been commercialized.

Finally, laser architectures outside of the red spectral region have been developed, but these systems sacrifice clinical efficacy because of the non-optimal wavelengths. For example, picosecond laser systems are available that produce 755 nm, near-infrared pulses using alexandrite as the lasing medium, as well as systems that using 532 nm picosecond pulses to pump a titanium sapphire oscillator, There is a need for dermatological picosecond laser systems that are able to efficiently remove tattoos that incorporate a variety of ink colors, particle sizes and ink depths, and which are relatively compact, non-bulky and easy to use. There is also a need for dermatological picosecond laser systems having a simplified construction with fewer components, which are capable of providing a variety of laser wavelengths for treatment of a wide variety of pigmentation conditions and skin conditions, and allow a user to switch from a first to a second treatment wavelength quickly and easily.

SUMMARY

In one embodiment, the present invention comprises a dermatological treatment system for removal of one or more of tattoos and pigmented lesions using pulsed laser light, comprising: a laser engine constructed and arranged to output first laser pulses having a first wavelength of from 1000 nm to 1200 nm, a first pulse width of 200 psec to 10 nsec, and a first pulse energy of from 100 mJ/pulse to 5 J/pulse; a second harmonic generator (SHG) constructed and arranged to receive the first laser pulses from the laser engine and generate second harmonic laser pulses having a second wavelength that is half the wavelength of the amplified laser pulses; an optical parametric oscillator (OPO) constructed and arranged to receive the second harmonic laser pulses and generate OPO signal pulses having a third wavelength of from 630 nm to 755 nm and OPO idler pulses having a fourth wavelength longer than the third wavelength; and an applicator constructed and arranged to receive and apply a selected one of the first laser pulses, the second harmonic laser pulses, and the OPO signal pulses to the skin of a patient.

In one embodiment, the present invention comprises a dermatological treatment system for treatment of at least one of a tattoo and a pigmented lesion using pulsed laser light at one of at least three selectable wavelengths, the system comprising: a laser engine constructed and arranged to output first laser pulses having a first wavelength of from 1050 nm to 1075 nm, a first pulse width of 200 psec to 1 nsec, and a first pulse energy of from 100 mJ/pulse to 5 J/pulse; a second harmonic generator (SHG) constructed and arranged to receive the pulsed laser light from the laser engine and generate second harmonic laser pulses having a second wavelength that is half the wavelength of the first laser pulses; an optical parametric oscillator (OPO) constructed and arranged to receive the second harmonic laser pulses as the pump input to the OPO and generate OPO signal pulses having a third wavelength of from about 630 nm to about 720 nm and OPO idler pulses having a fourth wavelength longer than the third wavelength; and an applicator constructed and arranged to apply one of the first laser pulses, the second harmonic laser pulses, and the OPO signal pulses to the skin of a patient, the applicator comprising a selector to select said one of the first laser pulses, the second harmonic laser pulses, and the OPO signal pulses.

In one embodiment, the present invention comprises an optical parametric oscillator (OPO) for use in a dermatological treatment system, wherein the OPO produces OPO signal pulses having a pulse width of from 200 psec to 1 nsec and a wavelength of from 630 nm to 720 nm, and OPO idler pulses having a fourth wavelength longer than the wavelength of the OPO signal pulses, the OPO comprising: an input coupler comprising a mirror having a high transmission (HT) at a pumping wavelength and a high reflectance (HR) at the OPO signal wavelength; a nonlinear crystal having a crystal length between 5 and 25 mm; and an output coupler comprising a mirror having a high reflectance (HR) at the pumping wavelength that transmits a selected portion of the OPO signal wavelength.

DESCRIPTION

Figure 1:
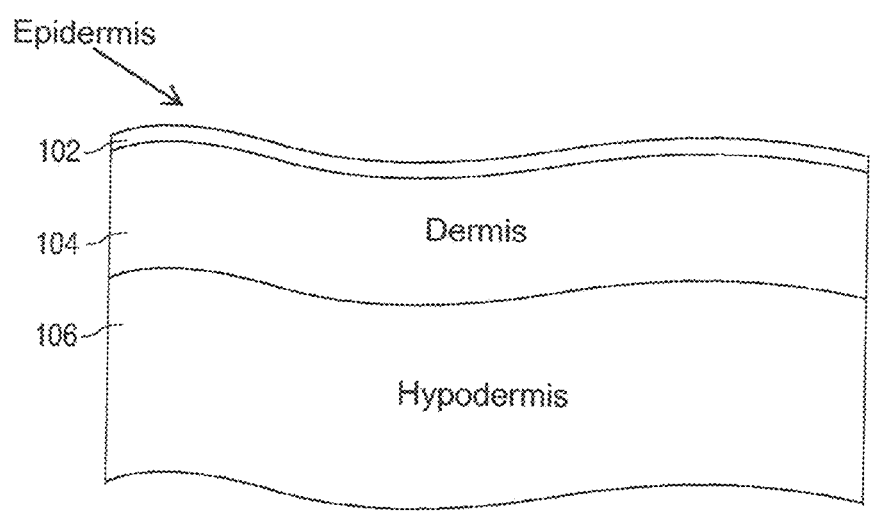
FIG. 1 is a cross-sectional illustration of skin tissue.

Exemplary embodiments of the present disclosure are illustrated in the drawings, which are illustrative rather than restrictive. No limitation on the scope of the technology, or on the claims that follow, is to be implied or inferred from the examples shown in the drawings and discussed here.

The present application discloses systems and methods for treatment of a variety of dermatological conditions using lasers, including systems providing a plurality of different wavelengths of laser light to provide improved therapies for certain skin pigmentation conditions, with at least one of the wavelengths being determined by an optical parametric oscillator. In some embodiments, systems of the present disclosure permit rapid adjustment from a first treatment wavelength to a second treatment wavelength.

Embodiments of the invention involve systems and methods for one or more of treating a pigmentation condition in human skin (including without limitation removal of tattoos and benign pigmented lesions) and skin resurfacing (including without limitation treatment of acne and other scar tissue) using pulsed laser light having a high peak power (i.e., power per pulse). Multiple wavelengths of laser light suitable for use in such systems and methods may be provided using an optical parametric oscillator (OPO).

In one aspect, a system capable of providing picosecond laser pulses at three or more different wavelengths suitable for treating pigmentation conditions and/or skin resurfacing is provided. In one aspect, a system capable of providing picosecond laser pulses at a plurality of wavelengths for treating pigmentation conditions and/or skin resurfacing using an OPO is provided. In one aspect, a system capable of providing high-energy, picosecond laser pulses at a plurality of wavelengths, including a red wavelength, is provided in a manner that allows a user to select one of the plurality of wavelengths quickly and easily.

In one aspect, a system capable of providing high-energy picosecond laser pulses at a red wavelength is provided in a manner that may be added to an existing picosecond laser system. In one aspect, a system for providing picosecond laser pulses at a red wavelength, capable of long-term operation without loss of output energy or beam uniformity is provided. In one embodiment, the system is capable of provided more than 1 million laser pulses without significant loss of output energy or beam uniformity. In one aspect, a tunable OPO capable of use in a dermatological picosecond laser system is provided that allows a user to select any desired wavelength within a range of 630-755 nm, preferably 630-720 nm, more preferably 660-680 nm, more preferably 665-675 nm, and more preferably about 670 nm.

In one aspect, methods for providing a dermatological treatment according to one of the foregoing systems is provided.

FIG. 1 is a side view illustrating a cross-sectional view of a portion 100 of the skin of a patient, including the outermost epidermis 110, the middle layer or dermis 120, and the bottom layer or hypodermis 130. The epidermis 110 has a thickness of about 80-100 μm, which may vary from patient to patient and depending on the area of the body. It includes up to five sub-layers and acts as an outer barrier. The outermost layer (the stratum corneum) consists of dead skin cells, which are constantly being replaced by new cells being made in the bottom layer (the stratum basale).

The dermal layer has thickness of about 1-5 mm (1000-1500 μm). The inks in a tattoo design and the melanin in a pigmented lesion are both located in the dermis. Consequently, laser light for removing tattoos and pigmented lesions must penetrate into the dermis. The dermis contains the blood vessels, nerves, hair follicles, collagen and sweat glands within the skin. Careful selection of a number of parameters must be made avoid damaging many of these structures in the design and construction of laser systems for removal of tattoos and pigmented lesions. For example, incorrect selection of the laser wavelength, pulse width, energy per pulse, the use (or nonuse) of a seed laser, or the pump energy of the laser source or amplifier may result in damage to one or more of the foregoing structures in the dermis, as well as poor performance in removal of the tattoo or pigmented lesion. Numerous other system choices, such as the use or non-use of an articulating arm for delivery of the laser light to a handpiece for application to the patient's skin, may also result in tissue damage and/or poor system performance if careful selection is not made.

The lowest layer of the skin is the hypodermis, which includes adipose tissue and collagen. The hypodermis helps control body temperature by insulating the structures of the body below the skin. In addition, the hypodermis protects the inner body tissues from damage by absorbing shock and impacts from outside the body. Because the hypodermis contains fat, its thickness varies widely from person to person based on diet, genetic makeup, and other factors.

Figure 2:
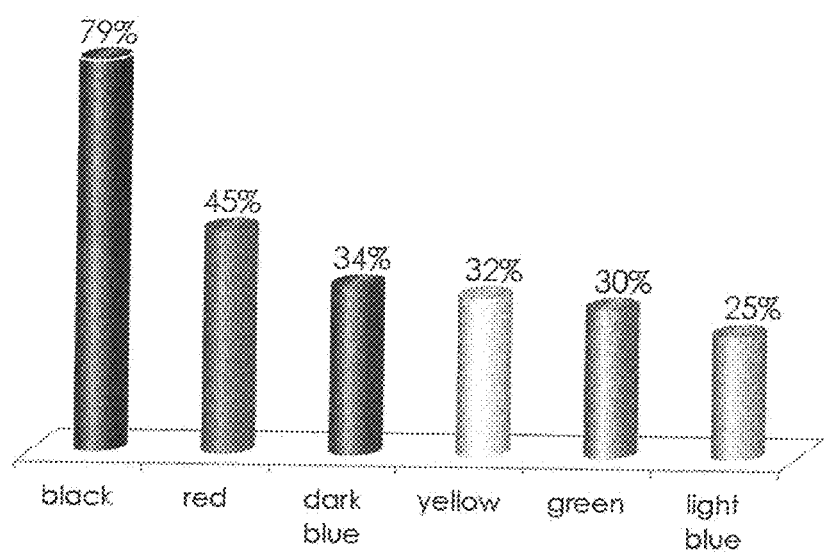
FIG. 2 is a graph illustrating the frequency of use of inks of various colors in tattoo designs.

FIG. 2 is a graph illustrating the frequency of ink use of certain colors in tattoo designs. Although black ink is the most frequently used color in tattoo designs (79% of tattoos), red ink is the next most frequently used color, appearing in about 45% of tattoo designs. Dark blue ink is used in about one third (34%) of tattoos, followed closely by yellow (32%) and green (30%) inks, respectively. Light blue ink is used in about one-fourth (25%) of tattoo designs.

Figure 3:
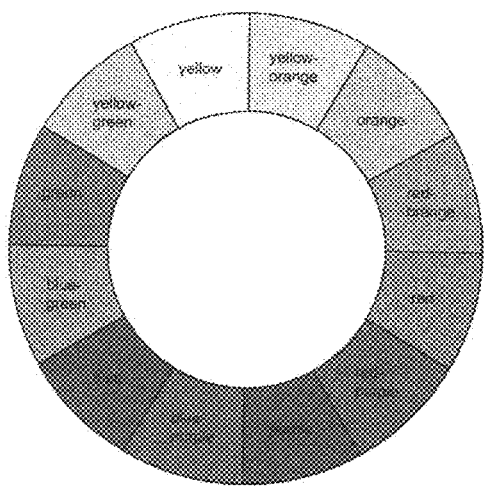
FIG. 3 is a color wheel illustrating various colors and their complementary colors.

FIG. 3 is a color wheel demonstrating the concept of complementary colors, which are the colors opposite to a given color on the color wheel. Thus, as previously noted, inks are more efficiently removed by laser light of a complementary color. Because of the prevalence of green and blue inks, it is desirable to have a system capable of reliably producing a red light wavelength in addition to the more widely available 1064 nm and 532 nm wavelengths.

The light absorbance profile of a substance is determined by the chromophores (i.e., the light-absorbing portions of molecules) within it that absorb light at particular wavelengths within the EMR spectrum. The color of a substance (e.g., skin) is determined by the absorbance profiles of the chromophores within the visible light portion of the EMR spectrum. Sunlight, although seen as a homogenous white color, is a composite of a range of different wavelengths of light in the ultraviolet (UV), visible, and infrared (IR) portions of the EMR spectrum. A substance appears to the eye as the complementary color of the light wavelengths that are absorbed.

Laser-based removal of pigmentation occurs by applying light at high fluences (i.e., energy per unit area) such that the chromophore-containing compounds within the pigmented area (e.g., ink particles in a tattoo or melanin in freckles or age spots) absorb so much energy that the ink or melanin particles in the pigmented area are ruptured or broken into small particles that may be removed by the body.

The more highly absorbed the wavelength of laser light by melanin (in the case of pigmented lesions) and/or inks (in the case of tattoos), the more efficient the removal. Stated differently, less energy must be delivered to rupture an ink or melanin particle if the wavelength of the laser light being used is highly absorbed by the ink in the tattoo or the melanin in the pigmented lesion. The absorption profile is only one aspect of laser wavelength selection, however, and a wide range of laser wavelengths are used to remove tattoos and pigmented lesions, including wavelengths in the visible and near-IR spectrum. Commercially available systems for removal of tattoos and pigmented lesions have used laser light at 532 nm, 597 nm, 650 nm, 755 nm, 785 nm, and 1064 nm, among others.

Figure 4:
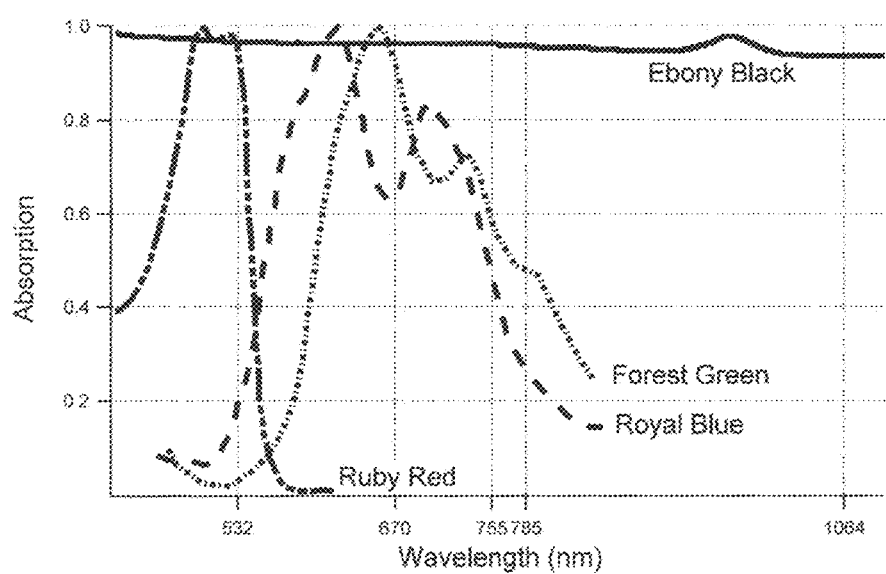
FIG. 4 is a graph illustrating the absorption spectra of red, green, blue, and black ink for various wavelengths of light.

FIG. 4 is a graph illustrating the absorption curves for various tattoo ink colors at a range of wavelengths. As previously noted, black ink ("ebony black") has a high absorbance across a wide range of laser wavelengths. Accordingly, black ink in tattoos may be efficiently removed using a variety of different laser systems and wavelengths.

FIG. 4 also shows that red ink ("ruby red") has a high absorbance at 532 nm and nearby wavelengths, but its absorbance falls rapidly at higher wavelengths. Consistent with the concept of complementary colors discussed earlier, the 532 nm wavelength corresponds with green light in the visible spectrum, which is the complementary color of red. Accordingly, red light may be removed efficiently by 532 nm green laser light but is poorly removed by, for example, 670 nm light in the red light portion of the visible spectrum.

Conversely, FIG. 4 shows that green ink ("forest green") has a high absorbance of 660-670 nm red light. Thus, tattoos with green ink are much more effectively removed by 660-670 nm laser light that, for example 532 nm green light, which is very poorly absorbed by green ink. Although green ink has a reasonable absorbance of near-infrared light at 755 and 785 nm (absorbance of about 0.6 and 0.5, respectively), it has more than 50% greater absorbance at 660-670 nm wavelengths (absorbance >0.9) in the visible red portion of the spectrum. Accordingly, 660-670 nm red laser light may provide for removal of green inks in tattoos with reduced laser intensity or fluence, fewer treatments sessions, or both, than green or near-infrared wavelengths.

FIG. 4 also illustrates that 660-670 nm red light will more efficiently remove blue inks ("royal blue") than near-infrared wavelengths such as 755 and 785 nm. Although not as strongly absorbing of red light as green inks, blue inks similarly show a much stronger absorption at a 670 nm wavelength than at 755 and 785 nm near-infrared (~40% greater absorbance than 755 nm wavelength and ~50% greater absorbance than 785 nm wavelength). Accordingly, 660-670 nm red light offers improved removal of blue inks than current widely used wavelengths.

Figure 5A:
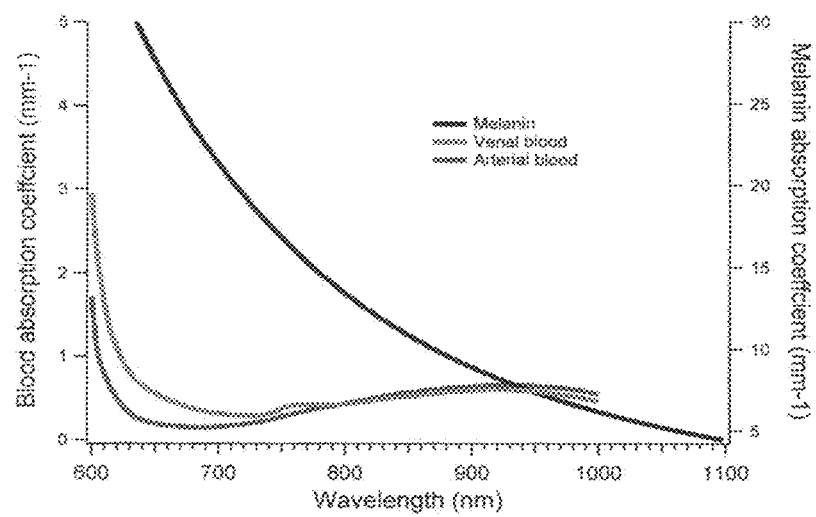
FIG. 5A is a graph illustrating the absorption coefficients of melanin, venous blood, and arterial blood for various wavelengths of light.

FIG. 5A is a graph illustrating the absorption curves for venal and arterial blood and melanin at various wavelengths of light. For removal of pigmented lesions, it is desirable to target melanin in the skin to the exclusion of other structures, notably blood and blood vessels. Greater safety may be provided by wavelengths that are poorly absorbed by non-target structures. FIG. 5A illustrates that melanin is strongly absorbent at lower wavelengths of light in the red visible wavelengths around 650, but its absorbance decreases steadily to a very low absorption in the near-infrared region. The absorbance of venous and arterial blood, on the other hand, decrease rapidly from 600 nm through about 650 nm. Arterial blood (lower curve) decreases rapidly until a relatively flat absorbance profile in the range of 630-700 nm, with a minimum value around 680 nm. Venous blood decreases rapidly to about 630-640 nm, then decreases more slowly to a minimum value at around 730 nm.

Maximum safety margin is provided at wavelengths having the maximum distance between the absorption curves of melanin on the one hand and venous/arterial blood on the other. This occurs between about 670 nm and about 700 nm, indicating that red laser light in this range will minimize damage to blood and blood vessels in the treatment of pigmented lesions. Thus, it would be desirable to add a red laser light capability to existing 1064/532 nm dermatological systems.

Figure 5B:
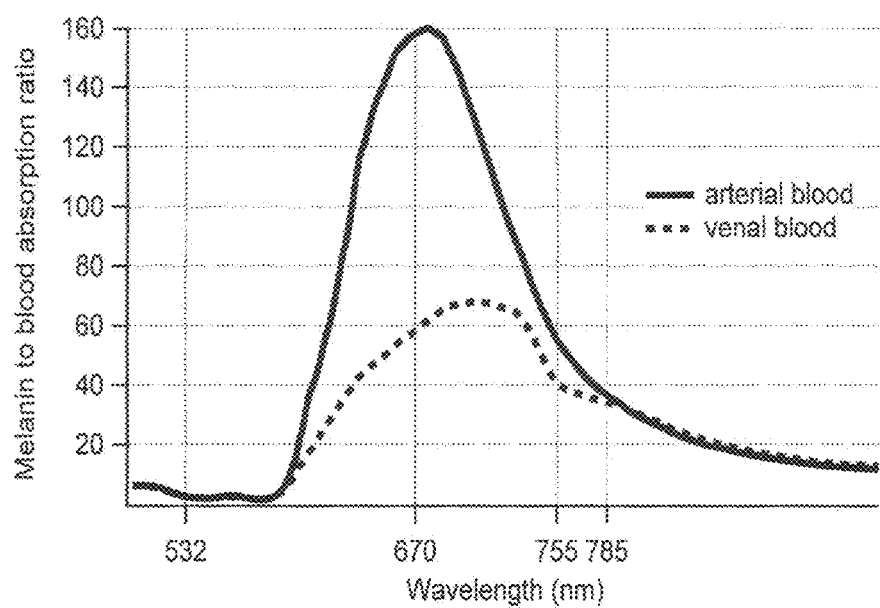
FIG. 5B is a graph illustrating the melanin to blood absorption ratio for venous and arterial blood for various wavelengths of light.

FIG. 5B illustrates this in another way by graphically indicating the ratio of the absorption ratios of venous and arterial blood to melanin. As the arterial blood curve demonstrates, melanin has its maximum absorption relative to arterial blood at a wavelength slightly above 670 nm. For venous blood, melanin reaches its relative peak at about 700 nm. Accordingly, red light in the 670-700 nm range, in addition to providing improved removal of green and blue tattoo inks, also offers potentially greater safety in removal of pigmented lesions.

In one embodiment, systems of the present invention may provide pulsed laser light at one or more wavelengths selected for efficient removal of tattoos having a wide range of ink densities. In one embodiment, a user may select a wavelength within a desired range for at least a portion of the wavelength output range that the system is capable of producing. In one embodiment, the laser pulses of the system have a pulse energy ranging from 100-1500 mJ/pulse. In one embodiment, the laser pulses of the system have a peak power of 250 megawatt (MW) or higher, preferably 500 MW or higher, more preferably 1 GW or higher. In one embodiment, a dermatological treatment system provides laser light at a fluence of up to 5.0 J/cm$^2$. In one embodiment, a user may select a spot size (e.g., by adjusting the diameter of a laser beam) for treating a pigmentation condition.

Some embodiments of the present invention involve high-energy pulsed lasers and an optical parameter oscillator (OPO) to provide a variety of selectable wavelengths for one or more of treatment of pigmentation conditions and skin resurfacing. Applicants have discovered that OPOs may be used to generate a range of pulsed laser wavelengths useful in removal of tattoos and benign pigmented lesions. Producing of such wavelengths using an OPO, however, requires a laser capable of producing relatively high-energy pulses. As used herein, the term "laser engine" refers to a pulsed laser system capable of producing pulses having a peak power of 250 megawatt (MW) or higher, preferably 500 MW or higher, more preferably 1 GW or higher.

Figure 6:
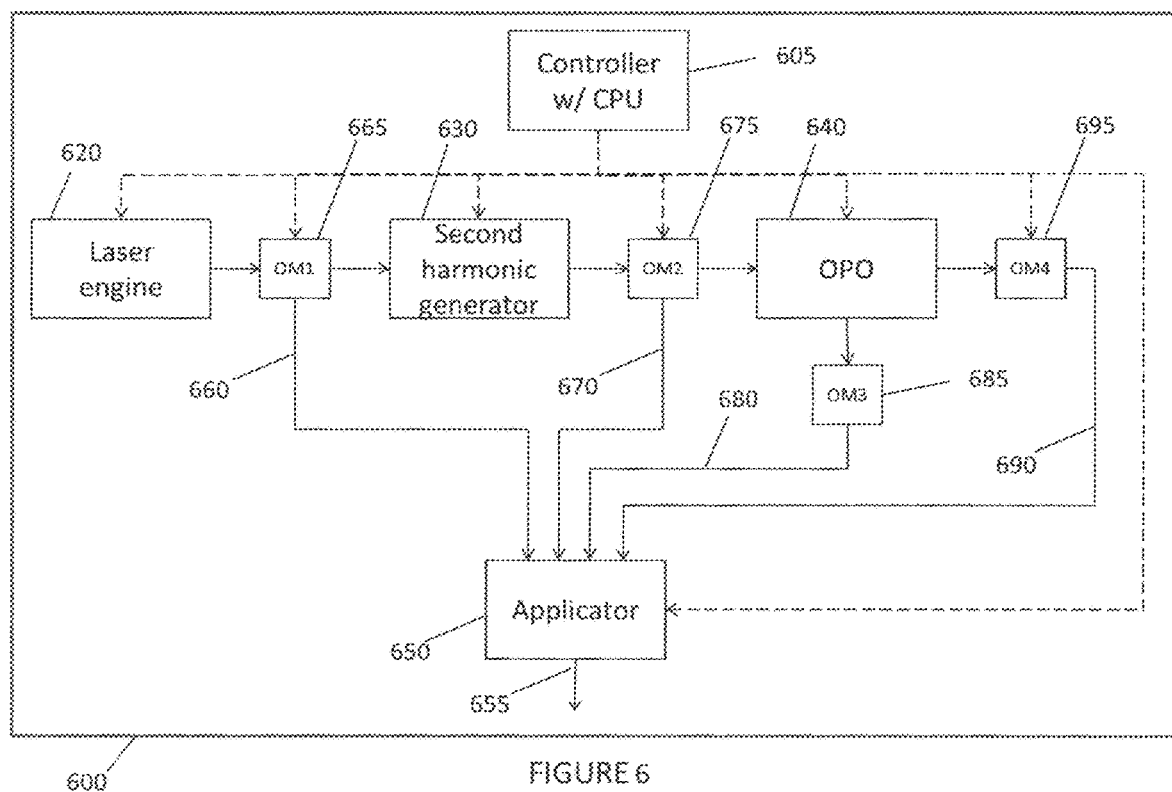
FIG. 6 is a block diagram of a system for treatment of dermatological tissue using pulsed laser light according to one embodiment of the present disclosure.

FIG. 6 is a schematic illustration, in block diagram form, of a dermatological laser treatment system 600 using high-energy pulsed laser light according to the present disclosure. A laser engine 620 is provided to produce high-energy pulsed laser light at a desired wavelength. Although a number of different laser engines are described in the present disclosure, the description herein of certain laser engines should not be construed as excluding others not specifically described. It will be appreciated by persons of skill in the art in view of the present disclosure that a variety of different materials, designs and techniques may be employed to generate high-energy pulsed laser light in systems of the present invention. Unless specifically excluded by the scope of the claims, all are considered to be within the scope of the present disclosure.

Laser engine 620 outputs laser pulses having a wavelength of from 1000 nm to 1200 nm, a pulse width (PW) of 200 psec to 10 nsec, and a pulse energy (PE) of 100 mJ/pulse to 5 J/pulse. In view of the fact that the peak power is given by the pulse energy divided by the pulse power or PE/PW, it will be appreciated that a variety of pulse widths and pulse energies may be used to produced high-energy laser pulses at a desired wavelength and having a peak power of 250 megawatt (MW) or higher. In one embodiment, laser engine 620 is a Q-switched laser.

A second harmonic generator (SHG) 630 receives the laser pulses from the laser engine 620 and generates second harmonic laser pulses with a wavelength that is half that of the pulses received from the laser engine 620. Many different crystals may be used for SHG, which results in an output signal having double the frequency and half the wavelength of the pumping signal. In the case of 1064 nm (fundamental) and 532 nm (second harmonic) wavelengths, potassium titanyl phosphate (KTP) and lithium tetraborate (LBO) are common choices, although other crystals such as potassium dihydrogen phosphate (KDP) may also be used. The crystals typically have a length between 2 and 15 mm. Depending on which material is chosen, the laser engine pulses received by the SHG may not require focusing to achieve efficient conversion to the second harmonic.

An optical parametric oscillator (OPO) 640 receives the pulses from the SHG and provides two pulsed laser outputs, known as the "signal" and "idler" respectively. Both OPO outputs (i.e., the OPO signal pulses and the OPO idler pulses) comprise laser light having a wavelength longer than the light received from the SHG 630. Optical parameter oscillators operate by receiving a pump laser signal (e.g., pulses as a first wavelength), which is used to induce parametric amplification within a nonlinear crystal in the OPO to produce the two output electromagnetic fields (i.e., the OPO signal pulses and the OPO idler pulses). OPOs are tunable over a wide range of wavelengths and potentially offer the ability to produce any desired wavelength within a range of desired wavelengths.

An applicator 650 is provided to receive pulsed laser light 655 from one or more of the laser engine 620, the SHG 630, and the OPO 640, and apply the received laser pulses to the skin of a patient for treating a pigmentation condition or skin resurfacing. The applicator may comprise a handpiece adapted to be held in the hand of a user, such as a physician or other healthcare provider, for treating the patient with pulsed laser light 655.

In some embodiments, the applicator may also comprise a selector (e.g., a touchscreen on the applicator) allowing a user to select the pulses from one or more of the laser engine 620, the SHG 630, the OPO (640) signal, and the OPO (640) idler for application to the skin of the patient. A first output path 660 is provided to direct the output of laser engine 620 to the applicator 650. In the embodiment of FIG. 6, first output path 660 comprises an optical multiplexer 665 between the laser engine 620 and the SHG 630 to direct the laser pulses from laser engine 620 to the applicator 650. A second output path 670 is provided to direct the output of the SHG 630 to applicator 650. In the embodiment of FIG. 6, an optical multiplexer 675 located between the SHG 630 and the OPO 640 directs the pulsed SHG output to the applicator 650. A third output path 680 is provided to direct the OPO signal output to the applicator 650. In the embodiment of FIG. 6, an optical multiplexer 685 located at the OPO signal output directs the OPO signal pulses to the applicator 650. In some embodiments, as shown in FIG. 6, a fourth output path 690 is provided to direct the OPO idler output pulses to the applicator 650. In the embodiment of FIG. 6, an optical multiplexer 695 located at the OPO idler output directs the idler output pulses to the applicator 650. In some embodiments, optical multiplexer 695 is omitted. In some embodiments (not shown) a single optical multiplexer and output path may be provided for both the OPO signal pulses and the OPO idler pulses.

In some embodiments, one or more of optical multiplexers 665, 675, 685, and 695 may be selectable by a user, e.g., by a rotatable mirror (not shown) from an interface located on the applicator 650, to allow the user to choose one among a plurality of available wavelengths of light to be routed to the applicator 650 to treat a patient. In addition, although the embodiment of FIG. 6 illustrates each of the first, second, third and fourth output paths, in alterative embodiments (not shown), one, two, or three of the four output paths shown may be omitted, such that pulses for one or more of the laser engine 620, the SHG 639, and the OPO 649 may not be available to treat a user. Although not shown in FIG. 6, one or more beam dumps may also be selectable by a user to shunt the laser pulses from one or more of the laser engine 620, the SHG 630, the OPO 640 signal output pulses, or the OPO 640 idler output pulses.

Although laser systems according to FIG. 6 may be constructed in a number of different physical layouts, a housing or chassis (not shown) may be used to provide store and protect some or all of the foregoing optical components. In one embodiment (not shown) a movable console (e.g., a wheeled cart) may function as a housing to house the laser engine 620, the SHG 630, the OPO 640, and the optical multiplexers 665, 675, 685, and 695. In one embodiment, an articulated arm having an optical medium (e.g., one or more waveguides) therein may be used to provide an optical path for the optical multiplexers 665, 675, 685, and 695 to direct pulses for a selected one of the laser engine 620, the SHG 630, the OPO 640 signal output, and the OPO 640 idler output pulses to the applicator (e.g., to a handpiece constructed and arranged to be held in the hand of a user). In one embodiment, a movable console may be provided as a housing to house the laser engine 620, SHG, and optical multiplexers 665 and 675, with the OPO 640 and optical multiplexers 685 and/or 695 located in an applicator such as a handpiece.

Finally, a controller 605 is provided, together with appropriate electrical circuitry, to control the operation of the dermatological laser treatment system of FIG. 6. In one embodiment, the controller 605 controls the operations, including the electrical operations, of one or more (and preferably all or most) of the laser engine 620, the SHG 630, the OPO 64, and applicator 650. In one embodiment, the controller 605 controls the operations of one or more of the laser engine 620, the SHG 630, the OPO 640, and multiplexers 665, 675, 685 and 695.

Laser engine 620 may comprise any of a number of designs to achieve stable, high-energy pulses, and all such designs are intended to be within the scope of the invention.

In one embodiment (not shown), laser engine 620 comprises a seed laser providing a pulsed initial laser signal for further amplification by an amplifier. Seed lasers are frequently used to produce a low power initial signal that may be amplified to obtain a final laser signal having desired characteristic. Many characteristics that may be desired in the final signal (e.g., short pulse widths, a wavelength having a narrow spectral line width) are easier to produce in a seed laser than in a single, high-power laser. The seed laser signal may then be easily amplified to obtain a laser signal having desired characteristics.

Although many seed lasers produce pulses having a pulse energy of 1 µJ or less, in one embodiment, a high-power seed laser is provided. The high-power seed laser is capable of producing pulses of at least 100 µJ per pulse, more preferably 100 µJ to 10 mJ, with a narrow linewidth and a wavelength of from 900-1200 nm, as well as a pulse width of 1 psec to 100 nsec. In one embodiment, the seed laser produces pulses having a stable polarity, and may be constructed and arranged to produce other desirable characteristics to enable the amplifier to output high-energy output pulses having a pulse energy of 100 mJ to 5 J, more preferably 500 mJ to 5 J, a wavelength of 1000-1200 nm, and a pulse width of 200 psec to 10 nsec. The pulses in seed laser have a relatively high peak power that may be amplified to obtain high-energy pulses as required by laser engine 620. In various embodiments, the seed laser may take the form of many oscillators known in the art to produce picosecond pulses including fiber lasers, microlasers, or diode lasers.

The pulsed output of the seed laser is received by an amplifier (not shown), which amplifies the output of the seed laser to produce amplified laser light having the same pulse width and wavelength as the seed laser, but with a greater pulse energy. In one embodiment, the amplifier amplifies the seed laser pulses by a factor of 1000 or more. The amplified laser pulses output from the amplifier may, in some embodiments, be output (e.g., to an applicator such as applicator 650) and used to treat a dermatological condition of a patient. Multiple approaches in the art are known for amplifiers that will amplify laser signals to a pulse energy of >100 mJ, including >500 MJ.

In one embodiment (not shown), laser engine 620 may comprise a high power oscillator. In one embodiment (not shown), laser engine 620 may comprise a hybrid mod-elocked laser combining the functions of a laser oscillator and amplifier into a single cavity. Other approaches may also be used to produce appropriate laser engines 620.

There are a number of challenges to producing an OPO capable of pulse energies of 50 mJ/pulse or greater for picosecond lasers. For optimized designs, the conversion efficiency of pump light to output (signal and idler) is about 30-50%. Because of the high energies involved, relatively large beam diameters must be used to avoid exceeding the threshold intensity to damage to optical structures within the OPO. In addition, the cavity length must be limited to enable the light to make at least 10-30 round trips across the cavity during the pulse duration (or width) to enable the signal and idler fields to build up to maximum energy. This results in a scaling law of about 1 cm/ns for the maximum cavity length vs. pump pulse duration. Thus, for a nanosecond laser having a pulse duration of 5 ns, the cavity length should be limited to 5 cm or less. For a picosecond pulse, the cavity length should thus be limited to less than 1 cm. However, it is not possible to simply make the cavity very small because cavity length is inversely related to beam quality, as explained below.

The combined constraints of large beam diameter and short cavity length imposed for achieving high pulse energies (50 mJ/pulse or greater) for picosecond pulses creates a fundamental challenge for OPO performance, because they result in the cavity having a high Fresnel number, expressed as $N=d^2/(4L\lambda)$, where N, d, L, and $\lambda$ are Fresnel number, beam diameter, cavity length and wavelength, respectively. Thus, because the Fresnel number varies inversely with the cavity length L, the smaller the cavity length, the larger the Fresnel number. It is well-known that optical cavities with $N\gg1$ are prone to lasing many transverse optical modes, and therefore have low beam quality.

Beam quality in laser systems is typically expressed as $M^2$, which provides a measure of the spatial coherence of the beam and therefore how well it can maintain collimation over a given distance. The larger the value of $M^2$, the higher the divergence angle of the beam (i.e., lower values indicate higher beam quality). The $M^2$ parameter is a critical measure for laser emission because it impacts the complexity of the optical delivery system design. For high energy picosecond medical laser systems requiring an articulated arm to deliver the beam to the applicator (e.g. a handpiece), the larger the value of $M^2$, the larger the diameter of the arm required to accommodate the divergence associated with the deterioration of the beam quality.

Figure 7:
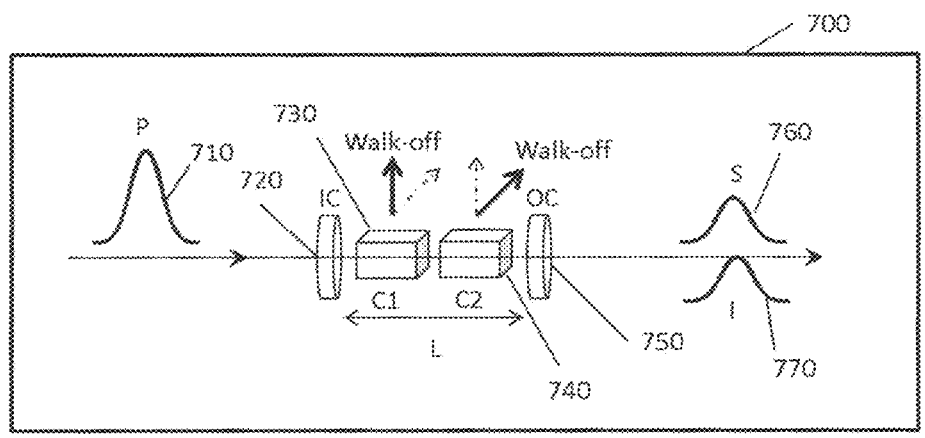
FIG. 7 is a block diagram of a prior art optical parametric oscillator suitable for use in dermatological treatment systems with nanosecond lasers.

An example of a proposed OPO design illustrates the problem. In an OPO design proposed by Rustad et al. (FIG. 7) loss of beam quality was addressed by using two nonlinear crystals C1 (730) and C2 (740) with orthogonally oriented beam walk-off axes and tuning of the signal wavelength to 670 nm to induce absorption of the idler pulses 770 in one of the crystals. The Rustad design proposes a 5 nsec pulse 710 having an input pulse energy of 120 mJ, a beam diameter of 6 mm, and a pulse wavelength of 532 nm. An input coupler mirror 720 is highly reflective (HR) at the 670 nm OPO signal wavelength and highly transmissive (HT) at the 532 nm pump or input wavelength. An output coupler 750 has high reflectance (HR) at the 532 nm pump wavelength and 35% reflectance at the 670 nm OPO signal wavelength, outputting OPO signal pulses 760 having a pulse energy of approximately 50 mJ. OPO 700 also produces idler pulses 770, shown in FIG. 7 for illustration as being output from output coupler 750 but which were, according to Rustad et al., absorbed within nonlinear crystals 730 and/or 740.

In simulations, Rustad et al. demonstrated that walk-off in orthogonal axes and absorption of the idler signal within the crystals 730, 740 may be combined to achieve a beam quality parameter $M^2 \approx 2$. Without idler absorption, the beam quality decreased to $M^2 \approx 8$. They also determined that the maximum efficiency is achieved when both crystals were 20 mm long. The cavity had a Fresnel number of N=335, indicating that the Rustad design significantly improved expected beam quality.

However, the Rustad et al. design is not well suited to use in picosecond laser systems. Applying the foregoing scaling law for a 750 psec pulse, the cavity is limited to less than 1 cm (about 0.75 cm in length), which is insufficient length to provide two nonlinear crystals of adequate length. More significantly, a 750 psec pulse increases the peak power of the pulse by a factor of 6 compared to a 5 nsec (5,000 psec) pulse. Thus, to keep the fluence the same and avoid damaging the optical components of the OPO, the beam area must also be increased by a factor of 6.6 and the beam diameter by a factor of 2.6. This would result in a cavity Fresnel number of N=9080 and a beam quality of $M^2>500$.

The present applicants have developed an OPO usable in picosecond laser systems that is adapted to overcome the limitations of conventional designs while maintaining high beam quality.

Figure 8:
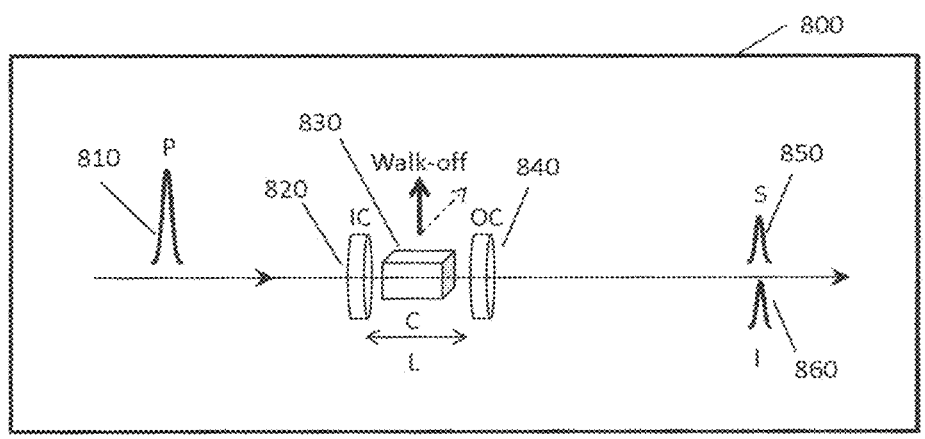
FIG. 8 is a diagram of one embodiment of the optical parametric oscillator of FIG. 6.

FIG. 8 is a schematic view of the optical elements of an optical parametric oscillator 800 according to one embodiment of the present invention. The OPO is adapted to be used in dermatological laser treatment systems having pulse energies of 50 mJ/pulse or higher. A pump laser providing pulses 810 is used to induce parametric amplification within a nonlinear crystal 830 to produce OPO signal pulses 840 and OPO idler pulses 850. The wavelengths of both the OPO signal pulses 840 and the OPO idler pulses 850 may be adjusted (or tuned) to achieve a desired wavelength with a wide range of possible wavelengths. Adjustments may be made, in different embodiments, by alteration of the crystal orientation (e.g., angle relative to the optical axis) or temperature.

For dermatological applications the ability to selectively damage target tissues or tissue structures is strongly determined by laser wavelength. Accordingly, embodiments according to the present disclosure offer the potential to select a desired wavelength within a wide range of available wavelengths to obtain the optimum wavelength for a particular target tissue or structure, in stark contrast to current dermatological approaches where the available wavelengths are limited to the atomic emission lines of the laser material being used and its harmonic wavelengths.

As already noted in connection with FIG. 6, in various embodiments of the invention the OPO 800 may be located in a console or housing, or in an applicator such as a handpiece. In some embodiments, the OPO 800 is located in the console or housing to enable wavelengths to be rapidly changed by a user and to enable the use of an articulated arm to deliver any of the available wavelengths to a single handpiece. The dimensions of typical articulated arms are about 15-20 mm ID and 1.5 meter length, and require a beam to have a beam quality of $M^2 \sim 100$ to avoid clipping the beam (because of beam divergence) inside the articulated arm. Accordingly, it is necessary to improve beam quality from $M^2>500$ to $M^2\sim 100$, without relying on multiple crystals or extending the cavity length beyond 10 mm.

The present invention provides those results in a single-crystal design that, contrary to prior designs, enables absorption of the OPO idler pulse wavelength within the OPO crystal to improve beam quality sufficiently to enable delivery through an articulated arm.

Referring again to FIG. 8, in one embodiment, nonlinear crystal 830 comprises a BBO (beta barium borate) crystal positioned between a pair of flat mirrors 820, 840 defining the OPO optical cavity. In one embodiment, a first mirror 820 serves as an input coupler and has high transmission (HT) at 532 nm and is highly reflective (HR) at the OPO signal wavelength, which in various embodiments may range from 575-750 nm, 620-720 nm, 660-680 nm, and about 670 nm. A second mirror 840 serves as an output coupler and transmits a portion of the signal wavelength. Second mirror 840 may be constructed to achieve a desired signal transmission from, e.g., 10-99%, preferably 25-75%, more preferably 40-60%, more preferably about 50%. The pump pulse width (or duration) may range from 1 psec to 1 nsec, preferably 100 psec to <1 nsec, more preferably 500-750 psec. In various embodiments, nonlinear crystal 830 may have a length of 5-25 mm, preferably 5-15 mm, and more preferably about 10 mm. In one embodiment, the pump beam has a diameter between 4 and In one embodiment, the pump beam has a diameter between 4 and 15 mm, more preferably about 10 mm.

The OPO 800 may have an efficiency of about 25% or higher, preferably 35% or higher. In one embodiment, OPO 800 is capable of receiving pump laser input pulses 810 at a wavelength of from 525-535 nm and having a pulse energy of 100 mJ/pulse to 5 J/pulse, and outputting OPO signal pulses 850 having a wavelength of from 620 nm to 720 nm and a pulse energy of about 50 mJ/pulse to about 2.5 J/pulse. In one embodiment, OPO 800 is capable of receiving pump laser input pulses 810 at a wavelength of from 525-535 nm and having a pulse energy of 100 mJ/pulse to 1 J/pulse, and outputting OPO signal pulses 850 having a pulse energy of about 25 mJ/pulse to about 500 mJ/pulse. In some embodiments, the OPO is capable of outputting both OPO signal pulses 850 and OPO idler pulses 860. In some embodiments, all or a portion of the OPO idler pulses are absorbed in the nonlinear crystal 830. In one embodiment, the nonlinear crystal may absorb from 10-75% of the OPO idler pulse energy, more preferably from 20-60% of the OPO idler pulse energy.

The signal and idler wavelengths $\lambda_s$ and $\lambda_i$ are related to the pump wavelength $\lambda_p$ by energy conservation through the equation $$\frac{1}{\lambda_p} = \frac{1}{\lambda_s} + \frac{1}{\lambda_i}$$

For a given pump wavelength, increasing the signal wavelength will decrease the idler wavelength and vice versa. In cases where optimization of the signal is desired, idler absorption may be used to reduce the $M^2$ of the signal (i.e., to improve signal quality) and the OPO may be adjusted to a signal wavelength where the idler experiences sufficient absorption to reduce the $M^2$ to support practical beam delivery to the patient surface. When the OPO is located within the housing of the system, an $M^2$ of ~100 is desirable to allow for a reasonably narrow arm diameter that such that the arm is ergonomic and not too costly. Even when the OPO is located in the applicator, it may be desirable to use idler absorption to help limit the $M^2$ in order to support a practical working distance and avoid the need for high numerical aperture optics within the applicator.

In one embodiment, BBO is used for the OPO crystal material since the transmission of BBO drops gradually from 100% at 2000 nm to <5% at 3500 nm. Using the equation above, we see that signal wavelengths from 630 to 730 nm will produce idler wavelengths of between 3420 and 1961 nm for a 532 nm pump. Higher idler absorption improves the $M^2$ but will also reduce the signal output energy. Therefore, a range of red wavelengths are possible and can be selected depending on the relative importance of signal pulse energy and $M^2$ for a given application. In on embodiment, transmission through an articulated arm facilitated by selection of 670 nm as the OPO signal wavelength, in which case the $M^2$ will be ~100 and single-pass idler absorption is ~30%.

In various embodiments, the present invention relates to the subject matter of the following numbered paragraphs.

100. A dermatological treatment system for removal of one or more of tattoos and pigmented lesions using pulsed laser light, comprising:
a laser engine capable of outputting first laser pulses having a first wavelength in the near-infrared region of the electromagnetic spectrum, a pulse width of 100 psec to 1 nsec, and a first pulse energy in the range of 100 mJ/pulse to 10 J/pulse;
a second harmonic generator (SHG) capable of receiving the first laser output pulses and generating second harmonic laser pulses having a second wavelength in the green region of the visible electromagnetic spectrum;
an optical parametric oscillator (OPO) capable of receiving the second harmonic laser pulses and generating OPO signal pulses having a wavelength in the red region of the visible electromagnetic spectrum and OPO idler pulses having a wavelength in one of the near-infrared and infrared regions of the electromagnetic spectrum; and
an applicator capable of receiving a selected one of the first laser pulses, the second harmonic laser pulses, and the OPO signal pulses and applying the selected pulses to the skin of a patient.

101. The dermatological treatment system of claim 100, wherein the second harmonic generator is capable of generating second harmonic pulses having a pulse energy in the range of from 50 mJ/pulse to 5 J/pulse.

102. The dermatological treatment system of claim 101, wherein the OPO is capable of OPO signal pulses having a pulse energy in the range of from 25 mJ/pulse to 2.5 J/pulse.

103. The dermatological treatment system of claim 101, wherein the laser engine, the SHG, and the OPO are capable of generating laser light pulses having a fluence of up to 5.0 J/cm$^2$.

104. The dermatological treatment system of claim 101, wherein the laser engine, the SHG, and the OPO are capable of generating laser light pulses having a fluence within the range of 3.0 J/cm$^2$.

The particular embodiments disclosed above are illustrative only, as the invention may be modified and practiced in different but equivalent manners apparent to those skilled in the art having the benefit of the teachings herein. Embodiments of the present invention disclosed and claimed herein may be made and executed without undue experimentation with the benefit of the present disclosure. While the invention has been described in terms of particular embodiments, it will be apparent to those of skill in the art that variations may be applied to systems and apparatus described herein without departing from the concept, spirit and scope of the invention. Examples are all intended to be non-limiting. It is therefore evident that the particular embodiments disclosed above may be altered or modified and all such variations are considered within the scope and spirit of the invention, which are limited only by the scope of the claims.

What is claimed is:

1. A dermatological treatment system for removal of one or more of tattoos and pigmented lesions using pulsed laser light, comprising:
a laser engine constructed and arranged to output first laser pulses having a first wavelength of from 1000 nm to 1200 nm, a first pulse width of 200 psec to 10 nsec, and a first pulse energy of from 100 mJ/pulse to 5 J/pulse;
a second harmonic generator (SHG) constructed and arranged to receive the first laser pulses from the laser engine and generate second harmonic laser pulses having a second wavelength that is half the wavelength of the amplified laser pulses;
an optical parametric oscillator (OPO) constructed and arranged to receive the second harmonic laser pulses and generate OPO signal pulses having a third wavelength of from 630 nm to 755 nm and OPO idler pulses having a fourth wavelength longer than the third wavelength;

an applicator constructed and arranged to receive and apply a selected one of the first laser pulses, the second harmonic laser pulses, and the OPO signal pulses to the skin of a patient;

a user-selectable first output path located between the laser engine and the SHG, wherein the user may select the first output path to output first laser pulses to the applicator;

a user-selectable second output path located between the SHG and the OPO, wherein the user may select the second output path to output second harmonic laser pulses to the applicator; and a user-selectable third output path located proximate the OPO signal output, wherein the user may select the third output path to output OPO signal pulses to the applicator.

2. The dermatological treatment system of claim 1, wherein the laser engine is selected from:
a) a seed laser and a seed laser amplifier, wherein the seed laser is constructed and arranged to output pulsed laser light having the first wavelength, the first pulse width, and a seed laser pulse energy of from 100 µJ/pulse to 5 mJ/pulse, and wherein the seed laser amplifier is constructed and arranged to receive the output of the seed laser and generate amplified laser pulses having the first wavelength, the first pulse width, and the first pulse energy; and
b) a hybrid modelocked laser.

3. The dermatological treatment system of claim 1, wherein the first wavelength is a wavelength of from 1050 nm to 1070 nm.

4. The dermatological treatment system of claim 1, wherein the second wavelength is a wavelength of from 525 nm to 535 nm.

5. The dermatological treatment system of claim 1, wherein third wavelength is a wavelength of from 630 nm to 720 nm.

6. The dermatological treatment system of claim 1, wherein third wavelength is a wavelength of from 660 nm to 680 nm.

7. The dermatological treatment system of claim 1, wherein the third wavelength is a wavelength of from 665 nm to 675 nm.

8. The dermatological treatment system of claim 1, wherein the OPO is adjustable such that a user may adjust the OPO signal pulses from the third wavelength of from 630 nm to 755 nm to a fifth wavelength of from 630 nm to 755 nm.

9. The dermatological treatment system of claim 1, wherein the third wavelength is from 630 nm to 720 nm and the fourth wavelength is from about 3420 nm to about 2037 nm, and wherein the OPO is adjustable such that a user may adjust the OPO signal pulses from the third wavelength of from 630 nm to 720 nm to a fifth wavelength of from 630 nm to 720 nm, and adjust the OPO idler pulses from the fourth wavelength of from about 3420 nm to about 2037 nm to a sixth wavelength of from about 3420 to about 2037 nm.

10. The dermatological treatment system of claim 1, wherein the OPO comprises:
a resonant cavity including a beta barium borate (BBO) crystal;
a first mirror coupled to a first end of the resonant cavity;
a second mirror coupled to a second end of the resonant cavity; and an adjustment element operable by the user to adjust the OPO output signal from a third wavelength to a fifth wavelength and adjust the OPO idler pulses from a fourth wavelength to a sixth wavelength by rotation of the BBO crystal.

11. The dermatological treatment system of claim 1, wherein the OPO is adjustable such that a user may select one of a plurality of OPO signal output wavelengths as the third wavelength, wherein each selectable OPO signal output wavelength produces a corresponding OPO idler wavelength as the fourth wavelength.

12. The dermatological treatment system of claim 1, wherein the applicator comprises a handpiece constructed and arranged to be held in the hand of a user and having an output to apply a selected one of the first laser pulses, the second harmonic laser pulses, and the OPO signal pulses to the skin of a patient, the system further comprising:
a housing, wherein the laser engine, the SHG, and the OPO are located within the housing; and
an articulated arm having a proximal end coupled to the housing and a distal end coupled to the handpiece, wherein one or more of the first laser pulses, the second harmonic laser pulses, and the OPO signal pulses is selectable to be delivered from the housing to the handpiece through an optical medium located in the articulated arm.

13. The dermatological treatment system of claim 1, wherein the applicator comprises a handpiece within which the OPO is located, the handpiece constructed and arranged to be held in the hand of a user and having an output to apply one or more of the first laser pulses, the second harmonic laser pulses, the OPO signal pulses, and the OPO idler pulses to the skin of the patient, the system further comprising:f
a housing, wherein the laser engine and the SHG are located within the housing; and
an articulated arm having a proximal end coupled to the housing and a distal end coupled to the handpiece, wherein one or more of the first laser pulses and the second harmonic laser pulses is selectable to be delivered from the housing to the handpiece through an optical medium located in the articulated arm.

14. The dermatological treatment system of claim 1, wherein the laser engine comprises a seed laser and a seed laser amplifier, wherein the seed laser is constructed and arranged to output pulsed laser light having the first wavelength, the first pulse width, and a seed laser pulse energy of from 100 µJ/pulse to 5 mJ/pulse, and wherein the seed laser amplifier includes a Nd:YAG crystal and amplifies the output of the seed laser by a gain of 10-1000.

15. The dermatological treatment system of claim 1, wherein the OPO includes a BBO crystal and produces an OPO signal output having a wavelength of from 620 nm to 755 nm.

16. The dermatological treatment system of claim 1, further comprising a controller to control the operation of one or more of the laser engine, the SHG, the OPO, and the applicator.

17. The dermatological treatment system of claim 1, wherein the SHG comprises a potassium dihydrogen phosphate (KDP) crystal.

18. The dermatological treatment system of claim 1, wherein the fourth wavelength is a wavelength of from 3420 nm to 1801 nm, and wherein the applicator is constructed and arranged to receive and apply a selected one of the first laser pulses, the second harmonic laser pulses, the OPO signal pulses, and the OPO idler pulses to the skin of a patient.

19. A dermatological treatment system for treatment of at least one of a tattoo and a pigmented lesion using pulsed laser light at one of at least three selectable wavelengths, the system comprising:
- a laser engine constructed and arranged to output first laser pulses having a first wavelength of from 1050 nm to 1075 nm, a first pulse width of 200 psec to 1 nsec, and a first pulse energy of from 100 mJ/pulse to 5 J/pulse;
- a second harmonic generator (SHG) constructed and arranged to receive the pulsed laser light from the laser engine and generate second harmonic laser pulses having a second wavelength that is half the wavelength of the first laser pulses;
- an optical parametric oscillator (OPO) constructed and arranged to receive the second harmonic laser pulses as the pump input to the OPO and generate OPO signal pulses having a third wavelength of from about 630 nm to about 720 nm and OPO idler pulses having a fourth wavelength longer than the third wavelength; and
- an applicator constructed and arranged to apply one of the first laser pulses, the second harmonic laser pulses, and the OPO signal pulses to the skin of a patient, the applicator comprising a selector to select said one of the first laser pulses, the second harmonic laser pulses, and the OPO signal pulses;
- a first output path located between the amplifier and the SHG, wherein the user may select the first output path using the selector to output first pulses to the applicator;
- a second output path located between the SHG and the OPO, wherein the user may select the second output path using the selector to output second harmonic laser pulses to the applicator; and
- a third output path located after the OPO, wherein the user may select the third output path using the selector to output the OPO signal pulses to the applicator.

20. The dermatological treatment system of claim 19, further comprising:
- a fourth output path located after the OPO, wherein the user may select the fourth output path using the selector to output the OPO idler pulses to the applicator.

21. The dermatological treatment system of claim 19, wherein the first wavelength is from about 1055-1070 nm, the second wavelength is from about 525-535 nm, and the third wavelength is from about 660-680 nm.

22. The dermatological treatment system of claim 19, wherein the OPO is adjustable such that a user may alter the OPO signal pulses from a third wavelength of from 630 to 720 nm to a fifth wavelength of from 630 to 720 nm.

23. The dermatological treatment system of claim 19, wherein the OPO comprises:
- a resonant cavity including a BBO crystal;
- a first mirror coupled to a first end of the resonant cavity;
- a second mirror coupled to a second end of the resonant cavity; and
- an adjustment element operable by the user to adjust the output of the OPO from a first signal pulse wavelength and a first idler pulse wavelength to a second signal pulse wavelength and a second idler pulse wavelength by rotation of the BBO crystal.

24. The dermatological treatment system of claim 19, wherein the fourth wavelength is a wavelength of from about 3420 to about 2037 nm.

25. The dermatological treatment system of claim 1, further comprising a selector for selecting one of
- the first output path to output first pulses to the applicator;
- the second output path to output second harmonic laser pulses to the applicator; and
- the third output path to output the OPO signal pulses to the applicator.

26. The dermatological treatment system of claim 25, wherein the selector comprises a touchscreen.

27. A dermatological treatment system for removal of one or more of tattoos and pigmented lesions using pulsed laser light, comprising:
- a laser engine constructed and arranged to output first laser pulses having a first wavelength of from 1000 nm to 1200 nm, a first pulse width of 200 psec to 10 nsec, and a first pulse energy of from 100 mJ/pulse to 5 J/pulse;
- a second harmonic generator (SHG) constructed and arranged to receive the first laser pulses from the laser engine and generate second harmonic laser pulses having a second wavelength that is half the wavelength of the amplified laser pulses;
- an optical parametric oscillator (OPO) constructed and arranged to receive the second harmonic laser pulses and generate OPO signal pulses having a third wavelength of from 630 nm to 755 nm and OPO idler pulses having a fourth wavelength longer than the third wavelength;
- an applicator constructed and arranged to receive and apply a selected one of the first laser pulses, the second harmonic laser pulses, and the OPO signal pulses to the skin of a patient;
- at least one output path selected from
  - a) a user-selectable first output path, wherein the user may select the first output path to output first laser pulses to the applicator; and
  - b) a user-selectable second output path, wherein the user may select the second output path to output second harmonic laser pulses to the applicator; and
- a user-selectable third output path located proximate the OPO signal output, wherein the user may select the third output path to output OPO signal pulses to the applicator.

28. The dermatological treatment system of claim 27, further comprising a selector for selecting one of
- a) the at least one of a user-selectable first output path and a user-selectable second output path, and
- b) the user selectable third output path.

29. The dermatological treatment system of claim 28, wherein the selector comprises a touchscreen.

* * * * *